(12) United States Patent
Seung

(10) Patent No.: US 6,907,767 B2
(45) Date of Patent: Jun. 21, 2005

(54) DROPPING TEST APPARATUS FOR MOBILE COMMUNICATION TERMINAL

(75) Inventor: Yong Ho Seung, Kyungki-Do (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 10/424,518

(22) Filed: Apr. 28, 2003

(65) Prior Publication Data
US 2004/0007047 A1 Jan. 15, 2004

(30) Foreign Application Priority Data
Jul. 13, 2002 (KR) .................. 10-2002-0041013

(51) Int. Cl.$^7$ .............. G01N 3/52; B25J 11/00
(52) U.S. Cl. .................... 73/12.06; 901/30
(58) Field of Search .............. 73/12.06, 12.13, 73/12.01, 12.04, 12.05, 12.07, 12.09, 12.11, 12.14; 901/30, 31

(56) References Cited

U.S. PATENT DOCUMENTS 6,508,103 B1 * 1/2003 Shim et al. ............ 73/12.06

* cited by examiner

Primary Examiner—Edward Lefkowitz
Assistant Examiner—T Miller
(74) Attorney, Agent, or Firm—Lee, Hong, Degerman, Kang & Schmadeka

(57) ABSTRACT

A dropping test apparatus for a mobile communication terminal is provided. The test apparatus comprises: a main body; a first group of fixed members attached to a first group of inclined surfaces formed on the main body for providing one or more distinct dropping orientations for a folder type mobile communication terminal in an open position; a second group of fixed members attached to a second group of inclined surfaces formed on the main body for providing one or more distinct dropping orientations for a folder type mobile communication terminal in a closed position.

18 Claims, 3 Drawing Sheets

DROPPING TEST APPARATUS FOR MOBILE COMMUNICATION TERMINAL

CROSS-REFERENCE TO RELATED APPLICATIONS

Pursuant to 35 U.S.C. § 119(a), this application claims the benefit of earlier filing date and right of priority to the Korean Application No. 2002-41013, filed on Jul. 13, 2002, the content of which is hereby incorporated by reference herein in its entirety.

BACKGROUND OF THE INVENTION

1. Field of the Invention

The present invention relates to a mobile communication terminal, and particularly, to a dropping test apparatus for a mobile communication terminal.

2. Description of the Related Art

A mobile communication terminal (hereinafter, referred to as 'terminal') is a portable device by which voice, message and image information can be transmitted/received through a wireless medium. Recently, terminals having multimedia function besides the simple voice transmitting/receiving function are being developed.

However, since the mobile terminals become thinner and lighter they have become more susceptible to damage or malfunction due to dropping. Therefore, manufacturer of the terminal should perform dropping test for the terminal when the terminal is manufactured, and the terminal having enough durability can be manufactured through data obtained from the dropping tests.

FIG. 1 is a lateral view of a dropping test apparatus for a mobile communication terminal in accordance with the conventional art.

As shown in FIG. 1, the dropping test apparatus for the conventional mobile communication terminal comprises a fixed frame 11; a motor 14 engaged to an upper end portion of the fixed frame 11; a guide 13 located between the motor 14 and the supporting surface 12 apart from a front side of the fixed frame 11 at a predetermined distance; a holder 15 for providing a dropping angle for the terminal 20; an absorber 16 for defining the dropping distance of the holder 15 and reducing the dropping shock between the holder 15 and collision surface 17.

As shown in FIG. 2, the holder 15 includes a main body 15a; three connection plates 15b–15d (fixed members) vertically formed at inclined planes having angles of 0°, 45°, and 90° for the main body 15a for connecting to the terminal 20; and a guide insertion hole 15e provided at one side of the main body 15a for inserting the guide 13.

Operations of the conventional dropping test apparatus for a mobile communication terminal will be explained.

First, the motor 14 is driven to lift the holder 15 to a predetermined height. One connection plate suited for a test surface of the terminal 20 is selected from the connection plates 15b–15d of the fixed holder 15 and then the test terminal 20 is fixed to the selected connection plate. At this time, the connection plate 15b attached to the inclined plane having an angle of 0° for the main body is used to test front and rear surfaces of the terminal, and the connection plate 15c attached to the inclined plane having an angle of 45° for the main body is used for an edge test of the terminal 20, and the connection plate 15d attached to the inclined plane having an angle of 90° for the main body is used to test upper, lower, and lateral portions of the terminal 20.

For example, if the terminal 20 is fixed to the connection plate 15b, the holder 15 is dropped along the guide 13. The holder 15 is vertically dropped to collide with the absorber 16 formed at a lower end of the guide 13. The terminal 20 is separated from the connection plate 15b as the result of colliding with the absorber 16 and drops on the collision surface 17. The absorber 15 prevents the holder 15 from dropping below a predetermined height, and relieves shock and noise generated at the time of colliding with the holder 15.

Subsequently, test surfaces of the terminal 20 for the dropping test are changed by using another connection plate 15c–15d, and said operations are repeatedly performed, thereby collecting data for damage and break down of the terminal 20 by the dropping.

The holder 15 is provided with three connection plates. The three connection plates have angles of 0°, 45°, and 90° for various surfaces of the main body of the holder 15, respectively. The connection plate having an angle of 0° for the main body provides a dropping pose for two surfaces such as a front portion and a rear portion of the terminal 20, and the connection plate having an angle of 90° for the main body provides a dropping pose for four surfaces such as an upper portion, a lower portion, and lateral portions. Also, the connection plate having an angle of 45° for the main body provides a dropping pose for testing shock exerted on a special edge.

The conventional dropping test apparatus for a mobile communication terminal provides a dropping pose for six surfaces and a special edge of the terminal by considering only a bar type terminal.

Accordingly, the conventional dropping test apparatus for a mobile communication terminal is most suitable for a dropping test of only a bar type terminal, not a folder type terminal which may drop with the folder opened. That is, a dropping pose of six surfaces in a state that the folder is closed and a dropping pose of six surfaces in a state that the folder is opened is not provided by the conventional dropping test apparatus for a mobile communication terminal.

SUMMARY OF THE INVENTION

In accordance with one aspect of the invention, an apparatus for dropping a test item comprises: a holder having one or more dropping orientations for dropping a test item from a predetermined height; a guide for guiding the holder toward a collision surface; and wherein the holder comprises a main body comprising one or more surfaces to which one or more fixed members corresponding to said one or more dropping orientations are attached, wherein a test item can be attached to one of said fixed members in an open position. In some embodiments, the test item is a folder type mobile communication terminal.

The holder may further comprise a guide insertion hole for slidably communicating with the guide. Each fixed member is attached to a respective surface, wherein each surface forms an angle with the collision surface for respectively providing one or more dropping orientations. The one or more fixed members are connection plates, or connection grips, or the like, for example.

In one or more embodiments, each of the one or more dropping orientations provide a dropping position for a particular side of a test item. The main body has at least first and second surfaces with respective angles of $\alpha 1$ and $\alpha 2$ wherein $\alpha 1$ is approximately equal to: (angle between inner surfaces of a folder type terminal in an open position—90°); and $\alpha 2$ is approximately equal to: (180°—angle between inner surfaces of a folder type terminal in an open position).

In one embodiment, the main body has at least third and fourth surfaces, respectively having angles of 0° and 90°. In another embodiment, the main body comprises at least first, second, third, and fourth surfaces with respective angles of α1, α2, α3 and α4 wherein: α1 is approximately equal to: (angle between inner surfaces of a folder type terminal in an open position—90°); α2 is approximately equal to: (180°— angle between inner surfaces of a folder type terminal in an open position); α3 is approximately 90°; and α4 is approximately 0°.

In accordance with another aspect of the invention, a dropping test apparatus of a mobile communication terminal comprises a main body; a first group of fixed members attached to a first group of inclined surfaces formed on the main body for providing one or more distinct dropping orientations for a folder type mobile communication terminal in an open position; a second group of fixed members attached to a second group of inclined surfaces formed on the main body for providing one or more distinct dropping orientations for a folder type mobile communication terminal in a closed position; and a guide insertion hole formed at one side of the main body, wherein the folder type mobile communication terminal can be attached to one of said fixed members.

The first and second fixed members in the second group are respectively attached to first and second surfaces of the main body, wherein the first and second surfaces respectively form 0° and 90° angles with a collision surface. Third and fourth fixed members in the first group are respectively attached to third and fourth surfaces of the main body, wherein the third and fourth surfaces respectively form respective angles of α1 and α2 with a collision surface, wherein: α1 is approximately equal to: (an angle between inner surfaces of a folder type mobile communication terminal—90°); and α2 is approximately equal to: (180°— an angle between inner surfaces of a folder type mobile communication terminal).

In accordance with one or more embodiments, an apparatus for dropping a test item comprises: means for holding a test item, in an open position, in one or more dropping orientations and for dropping the test item from a predetermined height; means for guiding the holding means to move in approximately vertical directions; and means for absorbing the impact from dropping the test item, wherein the test item is a folder type terminal.

The holding means comprises: a main body having a guide insertion hole for slidably communicating with the guiding means; wherein the main body has one or more surfaces to which one or more fixed members corresponding to said one or more dropping orientations are attached, wherein a test item can be attached to one of said fixed members. Each fixed member is attached to a respective surface, and each surface forms an angle with the collision surface for respectively providing one or more dropping orientations.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Reference will now be made in detail to preferred embodiments of the invention, examples of which are illustrated in the accompanying drawings.

Figure 1:
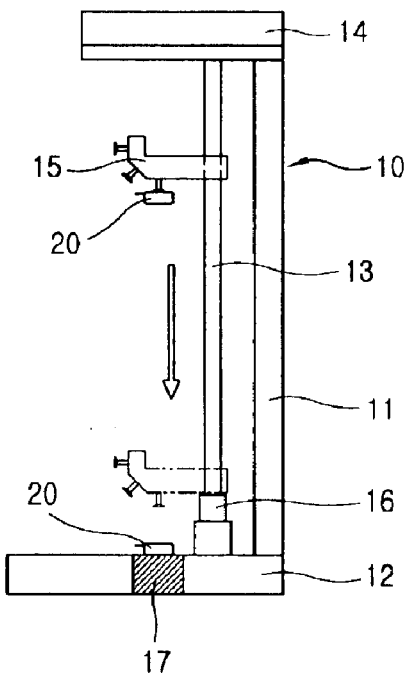
FIG. 1 is a planar view of a dropping test apparatus for a mobile communication terminal in accordance with the conventional art.
Figure 2:
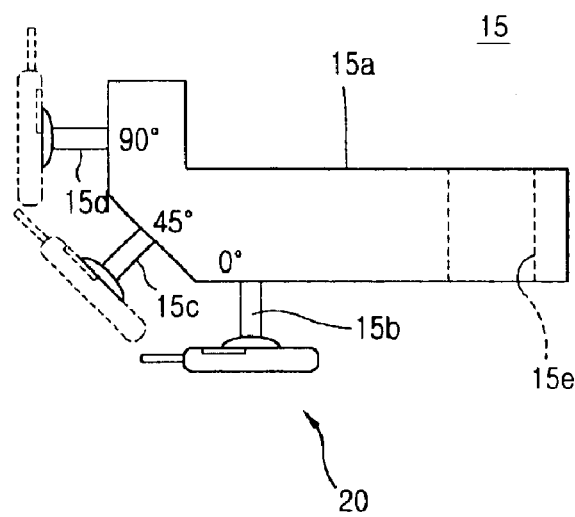
FIG. 2 is a detail view for a holder of FIG. 1.
Figure 3:
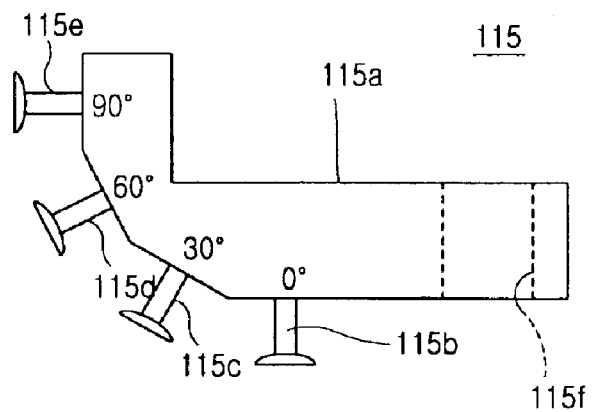
FIG. 3 shows a holder structure in a dropping test apparatus for a mobile communication terminal according to one embodiment of the invention.

Referring to FIG. 3, the dropping test apparatus for a mobile communication terminal according to one embodiment of the invention comprises: a main body 115a; a plurality of connection plates (e.g., 115b–115e) vertically formed at inclined planes having angels of approximately 0°, 30°, 60° and 90° in relation with a lower surface of the main body 115a; and a guide insertion hole 115f formed at one side of the main body 115a. The fixed members 115b–115e may comprise a plurality of connection plates or grips, in accordance with one embodiment, as shown.

Operations of the dropping test apparatus for a mobile communication terminal according to the present invention will now be explained.

Connection plates 115c and 115d, for example, form predetermined angles (α1, α2) with the horizontal surface of the collision surface, besides conventional angles of 0° and 90°. A terminal 20 may be fixed to the corresponding connection planes 15b–15e.

Angles (α1, α2) of the inclined planes are determined by the following equation, in accordance with one embodiment:

α1=angle of the folder in open position—an angle of a vertical inclined plane (e.g., 90°);

α2=an angle of a horizontal inclined plane (e.g., 180°)— angle of the folder in open position.

Figure 4:
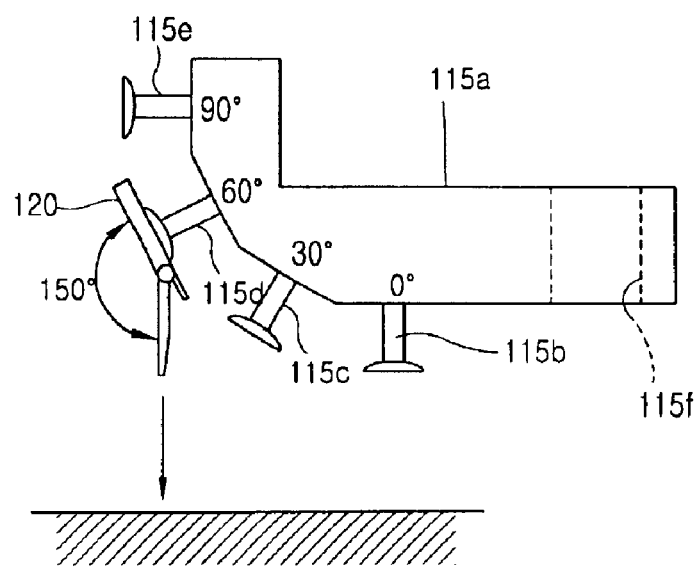
FIG. 4 illustrates one embodiment of the holder structure of FIG. 3 for providing a dropping pose of an upper end portion of a folder type terminal in an open position.
Figure 5:
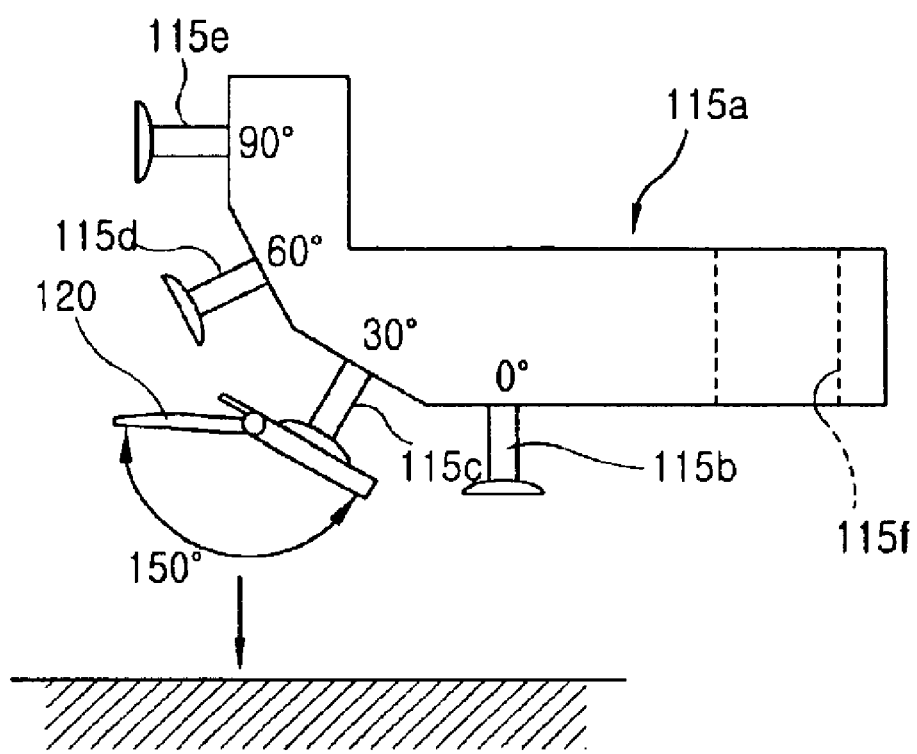
FIG. 5 illustrates one embodiment of the holder structure of FIG. 3 for providing a dropping pose of a front portion of the folder type terminal in an open position.

In some embodiments, the angle of the folder in open position is the angle formed between the inner surfaces of a folder type mobile communication terminal, when it is opened. Accordingly, as shown in FIGS. 4 and 5, in case that an opened angle of the folder is approximately 150°, the angles (α1, α2) of the inclined planes to which the connection plates (115c and 115d) are attached become approximately 30° and 60°, respectively by the said equation.

The approximate angles of 30° and 60° are devised to provide a dropping pose of an upper end portion and a front portion of the folder type terminal in a state that the folder is opened. Accordingly, in a case that the folder is closed, a dropping pose for various surfaces is provided by using the connection plates of approximately 0° and 90°. In case that the folder is opened, a dropping pose for various surfaces is realized by using the connection plates having angels of approximately 0°, 90°, 30° and 60° (115c and 115d).

At the time of a dropping test of the terminal 20, the motor 14 is driven to lift the holder 115 to a predetermined height. A suitable connection plate is selected from the plurality of connection plates (e.g., 115b–115e) according to the type of the terminal 20 (flip or folder) and their respective test surfaces, and then the terminal 20 is fixed to the selected connection plate to be vertically dropped.

The holder 115 vertically descends along the guide 13 and collides with the absorber 16. On impact, terminal 20 is separated from the connection plate and collides with a collision surface 12. Dropping test data of the folder type terminal is thereby accurately calculated for various dropping positions and angles.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. An apparatus for dropping a test item comprising:
   a holder having at least one dropping orientation for dropping the test item from a predetermined height; and
   a guide for guiding the holder toward a collision surface, wherein the holder comprises a main body comprising at least one surface to which at least a fixed member corresponding to said at least one dropping orientation is attached, wherein said at least one dropping orientation is configured so that the test item is attached to said at least one fixed member in an open position, wherein dropping the test item in said at least one dropping orientation results in a particular side of the test item to collide with a collision surface;
   wherein the test item comprises a folder type mobile communication terminal.

2. The apparatus of claim 1, wherein the holder further comprises a guide insertion mechanism for slidably communicating with the guide.

3. The apparatus of claim 1, wherein said at least one fixed member is attached said at least one surface, wherein said surface forms an angle with the collision surface to provide said at least one dropping orientation.

4. The apparatus of claim 3, wherein the main body comprises at least first, second, third, and fourth surfaces with respective angles of α1, α2, α3 and α4 wherein:
   α1 is approximately equal to: (angle between inner surfaces of a folder type terminal in the open position—90°);
   α2 is approximately equal to: (180°—angle between inner surfaces of a folder type terminal in the open position);
   α3 is approximately 90°; and
   α4 is approximately 0°.

5. The apparatus of claim 1, wherein the fixed member is a connection plate.

6. The apparatus of claim 1, wherein the fixed member is a connection grip.

7. The apparatus of claim 1, wherein each of the at least one dropping orientation provides a dropping position for a top edge of the test item.

8. The apparatus of claim 1, wherein the main body has at least first and second surfaces with respective angles of α1 and α2 wherein:
   α1 is approximately equal to: (angle between inner surfaces of a folder type terminal in the open position—90°); and
   α2 is approximately equal to: (180°—angle between inner surfaces of a folder type terminal in the open position).

9. The apparatus of claim 8, wherein the main body has at least third and fourth surfaces, respectively having angles of approximately 0° and 90°.

10. A dropping test apparatus of a mobile communication terminal comprising:
    a main body;
    a first group of fixed members attached to a first group of inclined surfaces formed on the main body for providing at least a first dropping orientation for a folder type mobile communication terminal in an open position;
    a second group of fixed members attached to a second group of inclined surfaces formed on the main body for providing at least a second dropping orientation for a folder type mobile communication terminal in a closed position; and
    a guide insertion portion formed at one side of the main body,
    wherein the folder type mobile communication terminal is attached to a member of at least one of said first group and second group of fixed members.

11. The apparatus of claim 10, wherein a first member and a second member in the second group of fixed members are respectively attached to a first surface and a second surface of the main body, wherein the first surface and the second surface respectively form approximately 0° and approximately 90° angles with a collision surface.

12. The apparatus of claim 10, wherein a third member and a fourth member in the first group of fixed members are respectively attached to a third surface and a fourth surface of the main body, wherein the third surface and the fourth surface respectively form angles of α1 and α2 with a collision surface, wherein:
    α1 is approximately equal to: (an angle between inner surfaces of the folder type mobile communication terminal—90°); and
    α2 is approximately equal to: (180°—the angle between the inner surfaces of the folder type mobile communication terminal).

13. The apparatus of claim 10, wherein the main body comprises at least first, second, third, and fourth surfaces with respective angles of α1, α2, α3 and α4 with a collision surface, to which first, second, third, and fourth fixed members are respectively attached, wherein:
    α1 is approximately equal to: (an angle between inner surfaces of the folder type mobile communication terminal—90°);
    α2 is approximately equal to: (180°—the angle between the inner surfaces of the folder type mobile communication terminal);
    α3 is approximately 90°; and
    α4 is approximately 0°.

14. The apparatus of claim 10, wherein at least one member in the first group and the second group of fixed members is a connection plate.

15. The apparatus of claim 10, wherein at least one member in the first group and the second group of fixed members is a connection grip.

16. An apparatus for dropping a test item comprising:
    means for holding the test item, in an open position, in a plurality of dropping orientations and for dropping the test item from a predetermined height;
    means for guiding the holding means to move in approximately vertical directions; and
    means for absorbing the impact from dropping the test item;
    wherein the test item comprises a folder type terminal.

17. The apparatus of claim 16, wherein the holding means comprises:
    a main body having a guide insertion mechanism for slidably communicating with the guiding means, wherein the main body has a plurality of surfaces to which at least a fixed member is attached, wherein each of the plurality of surfaces corresponds to one of the plurality of dropping orientations.

18. The apparatus of claim 17, wherein at least one fixed member is attached to each of the plurality of surfaces, and each of the plurality of surfaces forms an angle with the means for absorbing the impact, to respectively provide one of the plurality of dropping orientations.

* * * * *